United States Patent
Lopez, Jr. et al.

(10) Patent No.: US 6,440,406 B1
(45) Date of Patent: Aug. 27, 2002

(54) ATTRACTANT FOR MONITORING AND CONTROL OF ADULT SCARABS

(75) Inventors: Juan D. Lopez, Jr., College Station; Robert L. Crocker, Plano; Ted N. Shaver, College Station, all of TX (US)

(73) Assignees: The United States of America as represented by the Secretary of Agriculture, Washington, DC (US); The Texas A&M University System, College Station, TX (US)

(*) Notice: Subject to any disclaimer, the term of this patent is extended or adjusted under 35 U.S.C. 154(b) by 0 days.

(21) Appl. No.: 09/591,818

(22) Filed: Jun. 12, 2000

Related U.S. Application Data

(63) Continuation-in-part of application No. 09/166,655, filed on Oct. 5, 1998, now Pat. No. 6,074,634.
(60) Provisional application No. 60/061,005, filed on Oct. 6, 1997.

(51) Int. Cl.$^7$ .................. A01N 25/00; A01N 27/00; A01N 31/00; A01N 35/00; A01N 37/00; A01N 43/04; A01M 1/00
(52) U.S. Cl. .............. 424/84; 43/107; 424/405; 424/409; 424/410; 514/23; 514/159; 514/160; 514/163; 514/164; 514/532; 514/699; 514/717; 514/718; 514/730; 514/731; 514/763; 514/769; 514/770; 514/772; 514/772.3; 514/772.4; 514/777; 514/778; 514/781; 514/937; 514/949; 514/950; 514/957; 514/970
(58) Field of Search .................. 514/730, 717, 514/731, 693, 546, 729, 682, 681, 456, 640, 461, 159, 160, 161, 162, 163, 164, 530, 543, 544, 964, 965, 449, 512, 529, 532, 549, 645, 679, 690, 699, 701, 703, 724, 728, 733, 739, 762, 763, 764, 766, 769, 770, 772, 772.2, 772.3, 772.4, 772.7, 777, 778, 781, 949, 975, 718, 937–950, 957, 970, 23; 43/107; 424/84, 405, 409, 410

(56) References Cited

U.S. PATENT DOCUMENTS 5,202,124 A * 4/1993 Williams et al. ............ 424/405

FOREIGN PATENT DOCUMENTS

WO    WO 0019820    4/2000

OTHER PUBLICATIONS

Rearu, Barutaa Suaresu et al., "Attractants Containing Anilines and/or Benzoates for Control of Anomala Rufocuprea", *Chemical Abstracts*, 124:3062, 1996.

Landolt, Peter J., "Trapping the Green June Beetle (Coleoptera:Scarabaeidae) with Isopropanol", *5–Agrichemicals*, vol. 113, 1990, p. 253.

Leal, Walter Soares, et al., "Kairomone From Dandelion, *Taraxacum officinale*, Attractant for Scarab Beetle *Anomala octiescostata*", *Journal of Chemical Ecology*, vol. 20, No. 7, 1994, pp. 1697–1704.

Leal, Walter Soares, "Chemical Ecology of Phytophagous Scarab Beetles", *Annu. Rev. Entomol.*, 43, 1998, pp. 39–61.

* cited by examiner

*Primary Examiner*—Jose' G. Dees
*Assistant Examiner*—Frank Choi
(74) *Attorney, Agent, or Firm*—M. Howard Silverstein; Randall E. Deck; John D. Fado

(57) ABSTRACT

The present invention provides a composition for attracting scarabs. Liquid and solid formulations are provided, along with methods for their use, for controlling or eliminating scarabs, and/or protecting plants susceptible to scarab damage.

22 Claims, No Drawings

ATTRACTANT FOR MONITORING AND CONTROL OF ADULT SCARABS

CROSS REFERENCE TO RELATED APPLICATIONS

This application is a Continuation-In-Part of U.S. patent application Ser. No. 09/166,655, filed Oct. 5, 1998, now U.S. Pat. No. 6,074,634, which claimed the benefit of U.S. provisional patent application Ser. No. 60/061,005, filed Oct. 6, 1997, the contents of each of which are incorporated by reference herein.

BACKGROUND OF THE INVENTION

1. Field of the Invention

This invention relates to a novel composition and its use as an attractant for male, female or both sexes of scarab insect pests.

2. Description of the Prior Art

There are about 2,000 genera and 25,000 species in the beetle family Scarabaeidae in the world. In the U.S. and Canada alone, there are 1,395 and 135 genera. If the number of species and genera in the Americas is considered, the number would be considerably higher. One of the two groups in this family, the Pleurosticti, are called chafers. Adult chafers are strictly plant feeders on stems or roots, nectar, sap, or juice of ripening fruits and vegetables, fresh leaves, and flower nectar and pollen. These feeding habits lead to damage of ornamental and food crops. Adult females lay eggs primarily on the ground and the larvae, which are soil-dwelling white grubs, feed on living roots and can be very destructive in the urban and agricultural environments. Because of these soil dwelling habits, larvae are very difficult to control. Control efforts are then best directed at the adults before or while laying eggs, or the newly hatched larvae before they become established deeper in the soil. Appropriate timing of control efforts therefore requires real time information that can be derived from adult monitoring using traps on the level of adult activity. Efficacy of control measures would also be enhanced by directing these at the adults to preclude the need for direct treatment of areas in which eggs have been laid or larvae are hatching from the eggs. Thus, conventional control practices have usually involved high volume broadcast applications of insecticides on all infested areas. This trend has resulted in major concerns for environmental contamination and food safety among consumers.

Alternative control strategies involving the use of attract and kill technologies or attracticides, i.e., feeds/baits which are attractive and optionally toxic to the target insect species, for the adults have advantages over conventional practices for managing insect species. The availability of effective attracticides at action sites may have good potential for killing adults before they can disperse and reproduce in habitats. The successful development of attracticides and incorporation of this technology into adult management strategies will permit the reduction of insect pest problems over large areas, while substantially reducing the total use of synthetic pesticides and exposure of human foods to pesticide contamination. The development of effective attractants/attracticides will also be useful in monitoring populations of insect pests.

Various natural and synthetic attractants have been used with some success in attracticidal formulations to control and manage other scarab pest species. A review of sex pheromones and plant kairomones which have been investigated as attractants for a variety of different scarabs has been provided by Leal (1998, Chemical Ecology of Phytophagous Scarab Beetles, Annual Review of Entomology, 43:39–61). However, despite these advances, attractants effective for many agronomically important scarabs have yet to be developed.

SUMMARY OF THE INVENTION

We have now developed compositions which are effective as attractants for a number of economically important scarabs. This composition includes a mixture of effective amounts of one or more of the volatile compounds phenylacetaldehyde, methyl-2-methoxybenzoate, methyl salicylate, 2-phenylethanol, and limonene. The present invention also provides methods for a reduction in scarab species numbers or for their elimination, which includes attracting the insect species with the attractant composition. In the preferred embodiment, the attractant composition is used to pull the adult scarabs from the surrounding areas whereupon they may then be exposed to a lethal food source or other lethal preparation containing an insecticide, entomopathogen or other agent, possibly mixed with a feeding stimulant, on which the responding adults will feed or with which they will effectively make contact.

In accordance with this discovery, it is an object of the present invention to provide a composition effective as an attractant to scarabs.

Another object of the invention is to provide traps and controlled-release formulations containing the attractant composition.

A further object of the invention is to provide a method of reducing or preventing plant damage due to scarab species using the attractant composition in combination with a feeding stimulant and insecticide or with other mortality agents such as an entomopathogen which might not require ingestion.

Other objects, advantages and features of the invention will be readily apparent to one skilled in the art from the following description.

DETAILED DESCRIPTION OF THE INVENTION

The attractant compositions of the present invention are effective in attracting and controlling a number of agronomically important adult insects of the family Scarabaeidae (within the Order Coleoptera), commonly referred to as scarabs or scarab beetles. Scarabs of particular importance, which are attracted to the compositions, include those within the genera Phyllophaga, Cotinis, Diplotaxis, Cyclocephala, and Macrodactylus. Without being limited thereto, it is envisioned that the attractants of this invention may be used to attract and control species within these genera, including: *Phyllophaga anxia, P. rugosa, P. crinita, P. congrua, P. crassissima, P. obsoleta, P. ambigenus, P. brevidens, P. ravida, P. rugipennis, P. setifera, P. tumulosa, P. vetula, Cotinis nitida* (the green June beetle), *C. mutabilis, Macrodactylus subspinosus* (the rose chafer), *M. mexicanus, M. lineatus*, Diplotaxis species, *Cyclocephala comata*, and *C. lunulata*. Furthermore, the attractant compositions of this invention may be effective for attracting both sexes of adult scarabs. Since female beetles are the reproductive sex capable of laying eggs, the capture or kill of females could serve as a major tool in reducing succeeding populations.

Compounds effective for use as attractants herein include at least one, preferably two of the plant volatile components phenylacetaldehyde, methyl-2-methoxybenzoate, methyl salicylate, 2-phenylethanol, and limonene. However, while compositions of only one or two of these volatiles are attractive, generally efficacy is significantly improved by inclusion of three, four or preferably all five of these volatiles. Suitable formulations may be prepared from these volatiles in isolated or impure form. However, as a practical matter, it is expected that substantially pure volatiles will be formulated with an inert carrier (i.e., a carrier that is non-reactive with the above-mentioned volatiles) for use as an insect attractant composition. The practitioner skilled in the art will also recognize that these volatiles may be formulated or combined in a single composition or they may be provided in separate compositions, and they may be in liquid or solid form. It is understood that if formulated separately, the compositions should be positioned adjacent to one another during use. Liquid carriers for use herein include but are not limited to water or organic solvents, such as polyols, esters, methylene chloride, alcohol (such as $C_1$–$C_4$ alcohol) or vegetable oil, although vegetable oils and alcohols are preferred. Suitable vegetable oils include olive oil, sesame oil, peanut oil, canola oil, cottonseed oil, corn oil, soybean oil, mineral oil, as well as methylated forms of these oils, or mixtures thereof. Aromatic and linear hydrocarbon solvents may also be included. The active ingredient mixture may also be incorporated in a solid substrate, such as clays, diatomaceous earth, silica, polyvinyl chloride, polystyrene, polyurethanes, ureaformaldehyde condensates, and starches. Use of sintered polyethylene (either low or high voids) is particularly preferred. Other useful solid support matrices include expanded vermiculite and paraffinic or bees wax.

The amounts and concentrations of the volatile components, that is phenylacetaldehyde, methyl-2-methoxybenzoate, methyl salicylate, 2-phenylethanol, and limonene, are selected to provide an effective attraction of the target scarab. The effective amount is defined herein as that quantity of attractant that attracts the target insects to the location of a bait at a rate significantly higher than the attraction to a nonbaited location (i.e. negative control). Suitable amounts and concentrations of the volatile components may be readily determined by the practitioner skilled in the art, and may of course vary with the specific target insect, as well as its population density, the size of the area to be treated, environmental conditions such as temperature, humidity and wind, and the type of carrier or dispenser.

In a preferred embodiment, compositions for attracting the green June beetle, *Cotinis nitida*, include at least phenylacetaldehyde, more preferably with phenylethanol. However, greatest attraction is achieved by use of all five components. In Contrast, when attracting many species of Phyllophaga, preferred compositions include methyl-2-methoxybenzoate, alone or in combination with the other volatile components.

In another preferred embodiment, a composition of at least three of the volatiles are typically employed wherein the concentrations of the volatiles may vary between about 20–45% by weight phenylacetaldehyde, 0–30% by weight 2-phenylethanol, 0–30% by weight limonene, 15–40% by weight methyl-2-methoxybenzoate, and 5–25% by weight methyl salicylate. Particularly preferred concentrations of the volatiles (expressed as percent by weight) will be as follows: phenylacetaldehyde in an amount of about 20–30%, preferably about 20–25%, more preferably about 22–24%, and most preferably about 23%; 2-phenylethanol in an amount of about 20–30%, preferably about 20–25%, more preferably about :21–23%, and most preferably about 22%; limonene in an amount of about 20–30%, preferably about 22–26%, more preferably about 23–25%, and most preferably about 24%; methyl-2-methoxybenzoate in an amount of about, 15–25%, preferably about 18–22%, more preferably about 19–21%, and most preferably about 20%; and methyl salicylate in an amount of about 5–15%, preferably about 8–12%, more preferably about 9–11%, and most preferably about 10%. In one particularly preferred embodiment, the active ingredient mixture of the present invention contains approximately 23.51% by weight phenylacetaldehyde, 22.49% by weight 2-phenyl ethanol, 24.00% by weight limonene, 19.88% by weight methyl-2-methoxybenzoate, and 10.12% by weight methyl salicylate. In a further preferred embodiment, the active ingredient mixture of the present invention contains 5.77 mg/ml phenylacetaldehyde, 5.8 mg/ml limonene, 5.51 mg/ml 2-phenylethanol, 2.49 mg/ml methyl salicylate and 4.88 mg/ml methyl-2-methoxybenzoate. Limonene includes d- and l- forms as well as racemic mixtures.

The attractant composition may be further formulated with a variety of optional components or adjuvants, including but not limited to other plant volatiles, feeding stimulants, feed such as molasses, other insect attractants such as insect pheromones, or insect toxicants.

Yet other components which may be included in the formulation include humectants, preservatives, thickeners, antimicrobial agents, antioxidants, emulsifiers, film forming polymers and mixtures thereof. Additives which retard or slow the volatilization of the active mixture are preferred. Humectants may include polyols, sugars (such as molasses), glycols and hygroscopic salts. Antioxidants which protect the vegetable oils and reduce polymerization of phenyl acetaldehyde are preferred. Film forming polymers include gum rosin, latex, polyvinyl pyrrolidone, polyvinyl alcohol, polyvinyl chloride, polyethylene, polyvinyl acetate and mixtures thereof. Additional optional additives include, shellac, methyl methacrylate, and mixtures thereof.

In the preferred embodiment, feeding stimulants for the adult scarab beetles are included in the attractant composition and function to induce the target insects to contact and/or ingest the bait, particularly when formulated with an insecticide to effect control. Without being limited thereto, feeding stimulants such as fructose, fucose, glucose, and particularly sucrose, are preferred.

Another important component of the adult control system of the present invention is inclusion of insect toxicants or pesticides that are highly toxic to the adult insects, but do not significantly inhibit the attractance or feeding response when combined with a food source and applied to or in the vicinity (such as on plants or in a trap or bait station) of the crop plants treated with the feeding attractant.

Insect toxicants which may be included in the attractant composition (where it is consistent with their label) include but are not limited to insecticides such as carbaryl, methomyl, acephate, thiodicarb, cyfluthrin, malathion, chlorpyrifos, emamectin benzoate, abamectin, spinosad, endosulfan, and mixtures thereof. Bacterial, fungal, and viral or other pathogens may also be included, as well as insect growth regulators or compounds eliciting behavior modification or disrupting physiological functions. These may include, for instance, pigments and/or dyes which may mark, attract, modify various insect behaviors, or which may be toxic. Combination of the insecticide with the attractant composition of this invention and concentrated sucrose allows the use of significantly lower concentrations of insecticides to kill the adults under field conditions than would be used to control the insect pests with a normal commercial broadcast application of the same insecticides. Accordingly, one advantage of the present invention is a decrease in amount and concentration of insecticides required as compared with conventional insecticidal crop protection.

A variety of scarab pheromones are suitable for use with the attractant composition. Overviews of the pheromones for many insects, including scarabs, which may be used herein have been described, and include, for example, Mayer and McLaughlin (Handbook of Insect Pheromones and Sex Attractants, CRC Press, Boca Raton, Fla., 1991), Tamaki [Sex Pheromones, In *Comprehensive Insect Physiology Biochemistry and Pharmacology*, Vol. 9 Behavior, Kerkut and Gilbert (Ed.), Pergamon Press, New York, pp. 145–179], and Leal (1998, Chemical Ecology of Phytophagous Scarab Beetles, Annual Review of Entomology, 43:39–61), the contents of each of which are incorporated by reference herein.

Volatile or non-volatile extracts of Gaura or other plant species may also be included in. the attractant composition. Suitable volatiles include but are not limited to one or more, but less than. all, of the compounds selected from (E)-2-hexenal, (Z)-3-hexenol, (E)-2-hexenol, nonane, (Z)-3-hexenyl acetate, γ-terpinene, terpinen-4-ol, nerol, geraniol, eugenol, isoeugenol, γ-muurolene, valencene, 3,4-dihydro-8-hydroxy-3-methyl-1H-2-benzopyran-l-one, dodecyl acetate, methyl epijasmonate, 2-methylbutanal oxime, 2-methylbutanal (isomer A), 2-methylbutanal (isomer-B), cinnamaldehyde, benzyl alcohol, (E)-2-octenal, octanol, lilac aldehyde, an isomer of lilac aldehyde, lilac alcohol, an isomer of lilac alcohol, 2-phenyl-2-butenal, carvacrol, β-farnesene, α-selinene, selina-13,7(11)-diene, and benzyl benzoate, or mixtures thereof The attractant compositions may be used in a number of ways, including monitoring or controlling insect populations. In one preferred embodiment, the compositions may be placed within traps to monitor population changes. Precise monitoring will enable growers or other treatment applicators to apply insecticides near the time of maximum treatment efficacy and avoid insecticide application in situations where populations are low. In other preferred embodiments, the attractants may be used to control pest populations by employing large numbers of traps (trap-out strategy), or by combination with an effective amount of an insect toxicant or pesticide as described above to kill adult scarabs (as an attracticidal bait). Use in this manner should prove useful in suppressing target species before they can inflict damage to agronomically important crops.

In another embodiment, the attractant composition may be included as a part of traps or other solid supports which may also contain, be a part of or be in close proximity to a feeding stimulant, and/or an insecticide, pesticide, or other mechanical (such as a "bug zapper"), toxic or biologically active agent to eliminate, reduce, or prevent reproduction of the target insect species.

It is envisioned that the attractants may be used in conjunction with any type of appropriate trap or attractant disseminator as known in the art. The attractant can be applied or disseminated using a variety of conventional techniques, such as in an exposed solution, impregnated into a wicking material or other substrate, or incorporated in a dispenser similar to those sometimes used as deodorant dispensers. Further, the components of the attractant may be combined in a single dispenser provided within a single trap, or provided separately in a plurality of dispensers, all within a single trap. The attractant can be applied to the device undiluted, or formulated in an inert carrier. Volatilization can be controlled or retarded by inclusion of components as described above. Controlled, slow release over an extended period of time may also be effected by placement within vials covered with a permeable septum or cap, by encapsulation using conventional techniques, or absorption into a porous substrate.

One of ordinary skill will appreciate that the rate of release of the active ingredient mixture of the present invention may be varied by manipulation of the size of the reservoir and permeability of the matrix. The support or other delivery mechanisms of the present invention preferably provides release or volatilization of the active ingredient mixture of the invention for at least one week.

Application scenarios and methods of using the attractant composition of the present invention also include separate application of a feeding stimulant-insecticide mixture to plants by known methods with the placement of the attractant composition in a manner which will attract the scarab species to the feeding stimulant-insecticide mixture. Placement may include location in a strip in the same field which is upwind of the strip of the feeding stimulant-insecticide mixture. The attractant composition of the present invention may be applied in or on granules, plastic dispensers or wicks, for example, and may be applied parallel to sprays of a feeding stimulant-insecticide mixture. Cross-wind application may offer greater control of the insect population because of an increase in the area with effective volatile concentrations, and the foraging and ovipositing behavior in which the beetles fly upwind within the plant canopy. Single point application of the attractant composition may also be used effectively, depending on the existing wind conditions. Plants which may be protected from these scarab pests include but are not limited to agronomically important plants and crops such as turf grass, forage grass, corn (including field corn, seed corn, and sweet corn), horticultural flowers, sugar cane, and small grains, as well as fruit orchards and tree plantations or nurseries.

In the practice of any of the above-described embodiments, an attractant is used as a trap bait or is otherwise applied to the locus of or in the vicinity of infestation in an amount effective to attract the target insect. Factors such as population density, precipitation, temperature, wind velocity, and release rate will influence the actual number of insects trapped.

The following examples are intended only to further illustrate the invention and are not intended to limit the scope of the invention, which is defined by the claims.

EXAMPLE 1

The mixture of all five volatile components, prepared as described in Lopez et al. (U.S. patent application Ser. No. 09/166,655, filed Oct. 5, 1998) was evaluated as an attractant for scarabs. Evaluations using the mixture in traps were conducted at various sites at Dallas, Tex., adjacent to corn or cotton fields in an agricultural area SW of College Station, Tex., and in different habitats at various locations in Mexico. The primary trap used was the Trece Catch Can with a yellow top and a green catch container obtained from Trece, Inc., Salinas, Calif. At College Station only, wire cone traps originally designed to capture noctuid moths (Hartstack et al., *Jour. Econ. Entomol.*, 72:319–322, 1979) were also used in the evaluations. The traps were operated about 1 meter above ground level and were spaced at different distances based on the amount of space available in which to conduct the evaluations. Treatments were assigned to traps in trap lines either randomly or rotated every time the traps were checked to minimize trap location effects. Attractants for evaluation were dispensed primarily from sintered polyethylene to which the attractant was added until saturated. The sintered polyethylene was placed in various plastic containers to facilitate placing on the traps for evaluation. At College Station only, cotton dental wicks were used to dispense the attractants for evaluation by applying the attractants mixed with methylene chloride as a solvent. Traps were checked as appropriate based on the number of numbers of scarabs trapped.

Scarabs captured are shown in Table 1.

EXAMPLE 2

The volatile components were evaluated individually and in combination for efficacy for capturing scarabs. The evaluations were conducted as described in Example 1 near College Station, Tex., and Dallas, Tex., except that the volatile components were assayed individually as well.

The results are summarized below. In the College Station, Tex., data, the numbers represent the frequencies or number of incidents, over the course of the study, where more than one target insect was trapped (male and female, 4 repetitions). The Dallas, Tex., data represents the numbers of males/females captured. Abbreviations for the active agents tested are as follows: Mix M=five component mixture as described in Example 1, MMB=methyl-2-methoxybenzoate, MS=methyl salicylate, PA=phenylacetaldehyde, PE=2-phenylethanol, PEG=Japanese Beetle Lure, and SL=limonene.

| College Station, TX | |
|---|---|
| agent | Frequencies of trapping > 1 beetle |
| *Cotinis nitida* | |
| Mix-M | 65 |
| Anethol | 1 |
| MMB | 1 |
| MS | 0 |
| PA | 13 |
| PE | 2 |
| PEG | 7 |
| SL | 0 |
| *Euphoria sedpulcralis* | |
| Mix-M | 5 |
| Anethol | 0 |
| MMB | 0 |
| MS | 0 |
| PA | 1 |
| PE | 0 |
| PEG | 0 |
| SL | 0 |

| Dallas, TX | |
|---|---|
| agent | no. males/no. females |
| *Phyllophaga congrua* | |
| Mix-M | 1/2 |
| Anethol | 0/3 |
| MMB | 0/3 |
| MS | 4/0 |

-continued

| Dallas, TX | |
|---|---|
| agent | no. males/no. females |
| PA | 5/1 |
| PE | 5/2 |
| SL | 1/2 |
| *Phyllophaga crassissima* | |
| Mix-M | 14/12 |
| Anethol | 79/56 |
| MMB | 16/11 |
| MS | 6/10 |
| PA | 9/3 |
| PE | 8/5 |
| SL | 4/3 |
| *Phyllophaga crinita* | |
| Mix-M | 2523/0 |
| Anethol | 14/0 |
| MMB | 8627/7 |
| MS | 23/0 |
| PA | 16/1 |
| PE | 11/1 |
| SL | 32/3 |

EXAMPLE 3

The volatile components were evaluated in combination for efficacy for killing green June beetles, *Cotinis nitida*, in combination with a feeding stimulant/insecticide mixture. Evaluations were only conducted in cotton fields in an agricultural area SW of College Station, Tex. Previous evaluations with other insects as well as the capture of green June beetles in traps baited with attractants indicated the presence of the beetles in or the ability to attract large numbers into cotton fields in the area. Sections of cotton rows were marked off with flagging tape and left untreated or were treated with a feeding stimulant/insecticide mixture with or without the attractant. The attractant was dispensed from cotton dental wicks attached with wire ties to the top of cotton plants at 2 meter intervals down the row. The feeding stimulant/insecticide mixture consisted of liquid sucrose (67.5% sucrose in water) and 100 ppm weight:volume of the insecticide acephate. The feeding stimulant/insecticide mixture was applied with a carbon dioxide pressurized back-pack system using a modified spray gun for viscous paint. The morning after treatments were applied in the evening, the marked off treated and untreated area were checked and all dead beetles were collected and placed in zip-lock bags for identification. In some tests, the treated and untreated areas were checked in the afternoon and subsequent mornings after the treatments were applied to check for residual activity of the treatments. Beetles collected were counted and sexed to determine treatment effects.

The results of one test applied on a first day and checked at 11:00 am and 5:00 pm on the day after treatment showed that in 2 replicates of untreated and treated (attractant and feeding stimulant/insecticide), a total of 7 and 317 dead green June beetles were collected from the untreated and treated, respectively, at 11:00 am and 0 and 34 at 5:00 pm.

It is understood that the foregoing detailed description is given merely by way of illustration and that modifications and variations may be made therein without departing from the spirit and scope of the invention.

TABLE 1

| Genus | Species | Country |
|---|---|---|
| Anomala | cincta | Mexico |
| Anomala | flavipennis | U.S.A. |
| Anomala | foraminosa | U.S.A. |
| Anomala | inconstans | Mexico |
| Anomala | species | Mexico |
| Anomala | species | U.S.A. |
| Anomala | xantholea | Mexico |
| Callistethus | cupricollis | Mexico |
| Canthidium | species | Mexico |
| Canthon | cyanellus | Mexico |
| Cnemida | aterrima | Mexico |
| Copris | incertus | Mexico |
| Coprophanaeus | telamon | Mexico |
| Cotinis | mutabilis | Mexico |
| Cotinis | nitida | U.S.A. |
| Cotinis | species | Mexico |
| Cyclocephala | comata | Mexico |
| Cyclocephala | lunulata | Mexico |
| Cyclocephala | species | Mexico |
| Diplotaxis | sp. nr. puberea | Mexico |
| Diplotaxis | species | Mexico |
| Diplotaxis | turgidula | Mexico |
| Epectinaspis | mexicana | Mexico |
| Euetheola | rugiceps | U.S.A. |
| Euphoria | basalis | Mexico |
| Euphoria | leucographa | Mexico |
| Euphoria | sepulcralis | U.S.A. |
| Euphoria | species | U.S.A. |
| Euphoria | species | Mexico |
| Hoplia | sp. 1 | Mexico |
| Hoplia | sp. 2 | Mexico |
| Hoplia | species | Mexico |
| Hoplia | squamifera | Mexico |
| Macrodactylus | lineatus | Mexico |
| Macrodactylus | mexicanus | Mexico |
| Macrodactylus | species | Mexico |
| Onthophagus | gazella | U.S.A. |
| Onthophagus | sp. 1 | Mexico |
| Onthophagus | species | Mexico |
| Phyllophaga | ambygenus | Mexico |
| Phyllophaga | brevidens | Mexico |
| Phyllophaga | congrua | U.S.A. |
| Phyllophaga | crassissima | U.S.A. |
| Phyllophaga | crinita | U.S.A. |
| Phyllophaga | obsoleta | Mexico |
| Phyllophaga | ravida | Mexico |
| Phyllophaga | rugipennis | Mexico |
| Phyllophaga | setifera | Mexico |
| Phyllophaga | species | Mexico |
| Phyllophaga | tumulosa | Mexico |
| Phyllophaga | vetula | Mexico |
| Scatimus | ovatus | Mexico |
| Strigoderma | castor | Mexico |
| Strigoderma | festiva | Mexico |
| Strigoderma | mexicana | Mexico |
| Strigoderma | sp. nr. costulata | Mexico |
| Strigoderma | species | Mexico |
| Trigonopeltastes | species | Mexico |

We claim:

1. A method for attracting adult scarabs selected from the group consisting of Phyllophaga species, Cotinis species, Diplotaxis species, Cyclocephala species, and Macrodactylus species comprising providing one or more compositions of one or more volatile compounds selected from the group consisting of phenylacetaldehyde, 2-phenylethanol, limonene, methyl-2-methoxybenzoate, and methyl salicylate in combination with an inert carrier, to the locus of said scarabs, wherein said volatile compounds are present in an amount effective as a scarab attractant, and further wherein if said Cotinis species is *Cotinis nitida*, said composition comprises at least two of said volatile compounds.

2. The method as described in claim 1 wherein said scarabs are selected from the group consisting of *Phyllophaga anxia, P. rugosa, P. crinita, P. congrua, P. crassissima, P. obsoleta, P. ambigenus, P. brevidens, P. ravida, P. rugipennis, P. setifera, P. tumulosa, P. vetula, Cotinis nitida, C. mutabilis, Macrodactylus subspinosus, M. mexicanus, M. lineatus*, Diplotaxis species, *Cyclocephala comata*, and *C. lunulata*.

3. The method as described in claim 1 wherein said scarabs are selected from the group consisting of Phyllophaga species and Cotinis species.

4. The method as described in claim 1 wherein a single said composition comprising two or more of said volatile compounds is provided to the locus of said scarabs.

5. The method as described in claim 4 wherein one of said volatile compounds is methyl-2-methoxybenzoate.

6. The method as described in claim 4 wherein said composition comprises all of said volatile compounds.

7. The method as described in claim 1 wherein two or more of said compositions are provided adjacent to each other in the locus of said scarabs, and further wherein said compositions collectively comprise two or more of said volatile compounds.

8. The method as described in claim 7 wherein one of said volatile compounds is methyl-2-methoxybenzoate.

9. The method as described in claim 7 wherein said compositions collectively comprise all of said volatile compounds.

10. The method as described in claim 1 wherein said volatile compounds are substantially pure.

11. The method as described in claim 1 wherein said composition of said volatile compounds is provided in combination with an insect toxicant.

12. The method as described in claim 11 wherein said insect toxicant comprises an insecticide effective against said scarabs.

13. The method as described in claim 1 wherein said composition of said volatile compounds is provided in combination with a pheromone for one of said scarabs.

14. The method as described in claim 1 wherein said composition of said volatile compounds is provided in combination with a feeding stimulant.

15. The method as described in claim 14 wherein said feeding stimulant comprises a saccharide.

16. The method as described in claim 1 wherein said composition is positioned within an insect trap.

17. The method as described in claim 1 wherein said composition comprises a mixture of about 20–45% by weight phenylacetaldehyde, 0–30% by weight 2-phenylethanol, 0–30% by weight limonene, 15–40% by weight methyl-2-methoxybenzoate, and 5–25% by weight methyl salicylate.

18. The method as described in claim 17 wherein the concentration of phenylacetaldehyde is between about 20–30% by weight, the concentration of 2-phenylethanol is between about 20–30% by weight, the concentration of limonene is between about 20–30% by weight, the concentration of methyl-2-methoxybenzoate is between about 15–25% by weight, and the concentration of methyl salicylate is between about 5–15% by weight.

19. The method as described in claim 1 wherein said composition further comprises a humectant, antioxidant, preservative, emulsifier, film forming polymer or mixtures thereof.

20. The method as described in claim 1 wherein said carrier is selected from the group consisting of sintered polyethylene, clay, expanded vermiculite, wax, cellulose acetate, starch, hydrophobic polysiloxane, and mixtures thereof.

21. The method of claim 1 wherein said scarabs are selected from the group consisting of Phyllophaga species, Diplotaxis species, Cyclocephala species, and Macrodactylus species.

22. The method of claim 1 wherein said scarabs are a Cotinis species, and said composition comprises at least two of said volatile compounds.

* * * * *